United States Patent [19]

Gevins et al.

[11] Patent Number: 5,404,875
[45] Date of Patent: Apr. 11, 1995

[54] ELECTRODE ELECTROLYTE APPLICATION DEVICE

[75] Inventors: Alan S. Gevins, San Francisco; Donald Durousseau, Oakland, both of Calif.

[73] Assignee: SAM Technology, Inc., San Francisco, Calif.

[21] Appl. No.: 123,372

[22] Filed: Sep. 17, 1993

[51] Int. Cl.⁶ .............................................. A61B 5/04
[52] U.S. Cl. ............................... 128/635; 239/320; 222/386
[58] Field of Search ............... 128/639, 644, 731; 607/1, 2, 115, 153; 239/288.5, 320, 321; 222/386, 491, 494; 401/178

[56] References Cited

U.S. PATENT DOCUMENTS

| 808,635 | 1/1906 | Ciolfi et al. | 607/153 X |
| 4,683,892 | 12/1987 | Johansson | 128/639 |
| 4,800,888 | 1/1989 | Itil et al. | 128/644 |
| 5,273,037 | 12/1993 | Itil et al. | 128/644 |

Primary Examiner—Lee S. Cohen
Assistant Examiner—Jeffrey R. Jastrzab
Attorney, Agent, or Firm—Eliot S. Gerber

[57] ABSTRACT

An injector system to inject a bolus of electrolyte into EEG electrodes includes a pressure pump containing electrolyte and a pen-like injector which is filled from the pump for the injection of a bolus for each EEG electrode. The injector includes a finger-operated plunger having a piston, an electrolyte chamber, a hollow shaft portion of the plunger, and a flexible bottom portion having flaps which are spread open by the injector head (end of the plunger).

5 Claims, 3 Drawing Sheets

ELECTRODE ELECTROLYTE APPLICATION DEVICE

FIELD OF THE INVENTION

The present invention relates to medical devices and more particularly to devices for applying an electrolyte to electroencephalography (EEG) electrodes.

BACKGROUND OF THE INVENTION

At the present time electroencephalography (EEG), the detection and amplification of electrical brain waves, often uses a small number of electrodes, for example 4–12, which are removably secured to the scalp of the person being tested. A larger number of electrodes is used in the EEG "International 10/20 System".

It has been suggested that greater detail regarding brain wave activity may be obtained if a larger number of electrodes are used. The brain waves of a subject, after being amplified, digitized and analyzed in a computer system, may be displayed in a topological map. In such a map, brain wave activity in various areas is shown, for example, using a color scale. Such maps are more realistic and reliable if they are obtained from closely spaced sensors, i.e., from many EEG electrodes. Consequently, it has been argued that the preferred number of EEG electrodes is at least 64, and most preferably 128 or more.

At the present time, under some conditions, satisfactory and consistent results are obtainable with EEG electrodes by using an electrolyte (electrically conductive fluid), such as a solution or gel. The use of dry electrodes (without electrolyte) is often more convenient; however, dry electrodes often present problems in obtaining a constant low impedance contact with the scalp.

The use of an electrolyte also may present problems, as the fluid may have a tendency to spread over the scalp, possibly electrically shorting electrodes, and may be messy and difficult to remove. One type of EEG "wet" (electrolyte) electrode uses a small inverted cup-like structure which is filled with electrolyte by a technician before the electrodes are applied to the scalp. However, when the electrode set consists of a large number of electrodes (over 64), in a helmet, hat or web, the filling of the electrodes with electrolyte is time-consuming. Since that task takes so long, for example an hour, some of the electrodes may be missed and left without electrolyte.

The use of a large number (over 32) of EEG electrodes is discussed in U.S. Pat. No. 4,736,751 entitled "Brain Wave Source Network Location Scanning Method And System", which mentions the use of as many as 256 electrodes.

The use of conductive fluid or gel on EEG electrodes is shown in prior patents. In U.S. Pat. No. 4,595,013 entitled "Electrode Harness" conductive gel is applied to foam 58 within reservoirs 56. In U.S. Pat. No. 4,709,702 entitled "Electroencephalographic Cap", electrolyte is pumped from pump 60 through tube 50 to the area of penetration of the probe 31 (electrode). U.S. Pat. No. 4,537,198 entitled "Electrode Cap" uses an electrode having a washer-like foam pad 60 and a central opening through which passes a "semi-liquid or paste-like" electrolyte. In U.S. Pat. No. 4,683,892 entitled "Method And Apparatus For Conducting Brain Function Diagnostic Test", an electrolyte solution is fed through conduit 53 and the open lower end of a contact 50A to permit introduction of the electrolyte directly on the scalp of the person being tested.

SUMMARY OF THE INVENTION

In accordance with the present invention, there is provided a device and method for rapidly filling the cavities of EEG electrodes with a measured and predetermined quantity ("bolus") of an electrolyte. Using this device, a technician may fill 128 electrodes in less than 15 minutes, without having the electrolyte spread onto the outside of the electrodes or the cap and with a predetermined bolus of electrolyte deposited within each electrode, providing electrical contact between the scalp and electrode disk surface.

The system consists of an external reservoir of sufficient size to hold the electrolyte for 128 electrodes and a hand-operated pump to cause the electrolyte to flow from the reservoir to a hand-held pen-like electrolyte injector. The injector is provided to inject a predetermined quantity (bolus) of electrolyte (conductive fluid) into an electrode, such as an EEG electrode. The injector has a tubular casing having an inlet valve. The casing forms an internal electrolyte reservoir. A hand-operated plunger applies pressure to the electrolyte in the reservoir, a portion of the plunger being a hollow shaft portion having openings therethrough. When the plunger is depressed, electrolyte is carried from the internal reservoir by the tube portion of the plunger and flows out the bottom open end ("injector head") of the tube.

The injector has a cylindrical body with a relatively rigid top portion and a flexible bottom portion. The plunger protrudes through a hole at the top of the top portion and the bottom portion has four flexible flaps, forming a normally closed valve. The flaps are spread open, on top of the scalp, in order to part the hair, allowing electrolyte to contact the scalp.

When the plunger is depressed, the piston is pushed down on a block member fixed to the top portion. At the same time the injector head, at the free end of the hollow shaft portion, spreads open the flaps and the electrolyte flows at a rate proportional to the pressure on the piston, from the shaft portion out of the head portion orifice and into the electrode.

DETAILED DESCRIPTION OF THE DRAWINGS

Figure 1:
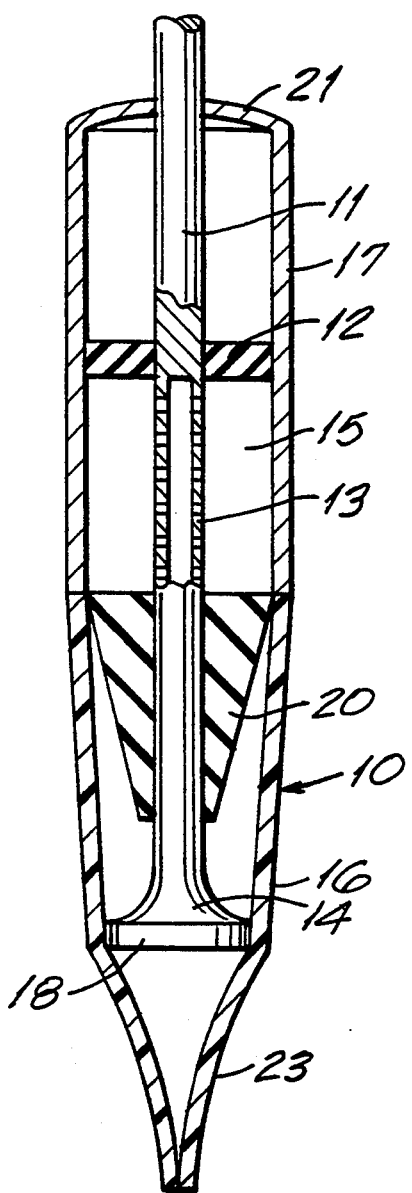
FIG. 1 is a side cross-sectional view of the injector device of the present invention with the plunger in the raised position.

As shown in FIG. 1, the electrolyte injector of the present invention includes a cylindrical body 10 having a top portion 17, preferably of a suitable metal or plastic material, forming an enclosed electrolyte chamber 15. The body 10 encloses a portion of a cylindrical plunger 11 having a piston head 12 fixed at its middle portion, the piston head being of rubber or other elastomeric material. The plunger 11, below head 12, has a hollow shaft portion 13 having holes therein of sufficient size to permit the flow of electrolyte therethrough.

Some suitable electrolytes are:
"ELECTRO-GEL" (TM, Electro Cap International);
"MEDI-TRACE EEG SOL" (TM, Graphic Controls);
"EMG GEL" from The Electrode Store;
"SPECTRA 360" (TM, Parker); and
"SAM BRAND" (TM, SAM Technology, Inc.)

The bottom end of the plunger 11 is flared outwardly to form an injector head 14 having an orifice 18 therein.

The bottom portion 16 of the body 10 is a flexible cylindrical member, preferably of a plastic material. The bottom portion 16 has a number of spreadable flaps 23, preferably four, which are spread open by the injector head 14.

A block member 20 having a hole for the plunger 11 to pass therethrough is fixed to the top portion 17. The top portion 17 has an upper cap-like flange 21 forming a hole for the plunger 11.

Figure 2:
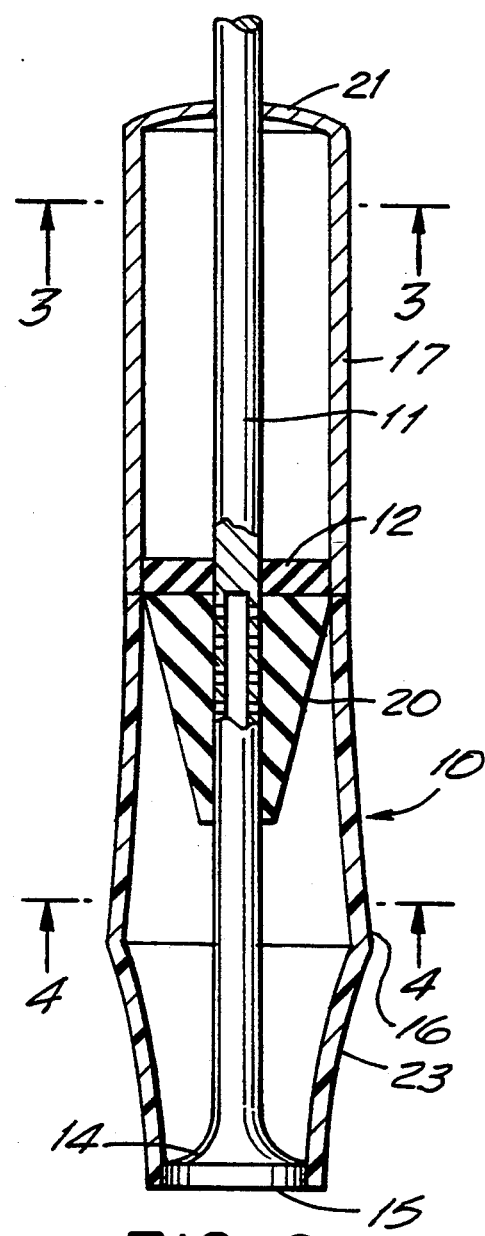
FIG. 2 is a side cross-sectional view of the injector device of FIG. 1 with the plunger in the depressed position.

In operation, as shown in FIG. 2, the plunger 11 is withdrawn and the chamber 15 fills with the fluid electrolyte.

Figure 3:
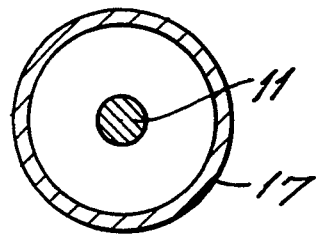
FIG. 3 is a cross-sectional view along line 3—3 of FIG. 2.
Figure 4:
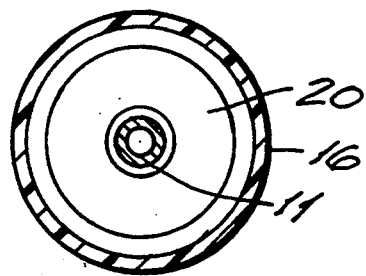
FIG. 4 is a cross-sectional view along line 4—4 of FIG. 2.

When the EEG electrode is to be filled with electrolyte, the flaps 23 are placed in the electrode and electrode holder cavity and the plunger 11 is depressed by the user. The plunger, as shown in FIG. 3, will move downward and its injector head 14 will spread out the flaps 23 parting the hair. As the piston head 12 moves downwardly, electrolyte will flow into the hollow shaft 13 and will flow out of the injector head orifice 18 into the EEG electrode holder filling the gap between the electrode and scalp surface. The injector head 14 is withdrawn (pulled upright), closing the flaps 23, and the injector 10 is withdrawn from the electrode.

When the plunger 11 is depressed, the electrolyte will not flow out of the holes in the hollow shaft portion 13 because those holes are closed by the block member 20, as shown in FIG. 2.

The amount of electrolyte in each deposit is predetermined by the size (length and diameter) of the electrolyte reservoir 15 and the hollow shaft 13.

Figure 5:
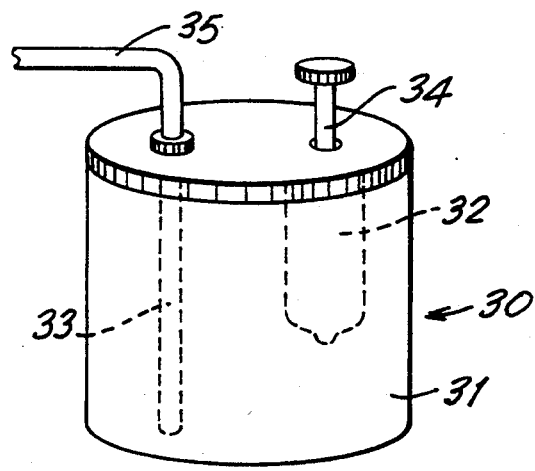
FIG. 5 is a side view of the electrolyte pump system.

The injector 10 may be filled with electrolyte in various ways. For example, a suitable pump system 30 is illustrated in FIG. 5. The pump system 30 includes a closed reservoir (container) 31 containing sufficient electrolyte to fill all the electrodes of interest, for example, sufficient electrolyte to fill 128 electrodes. A hand-operated plunger 34 applies air pressure through the one-way air valve of pump mechanism 32. The air pressure forces the liquid electrolyte out through the dip tube 33 and its connected electrolyte fill line 35.

Figure 7:
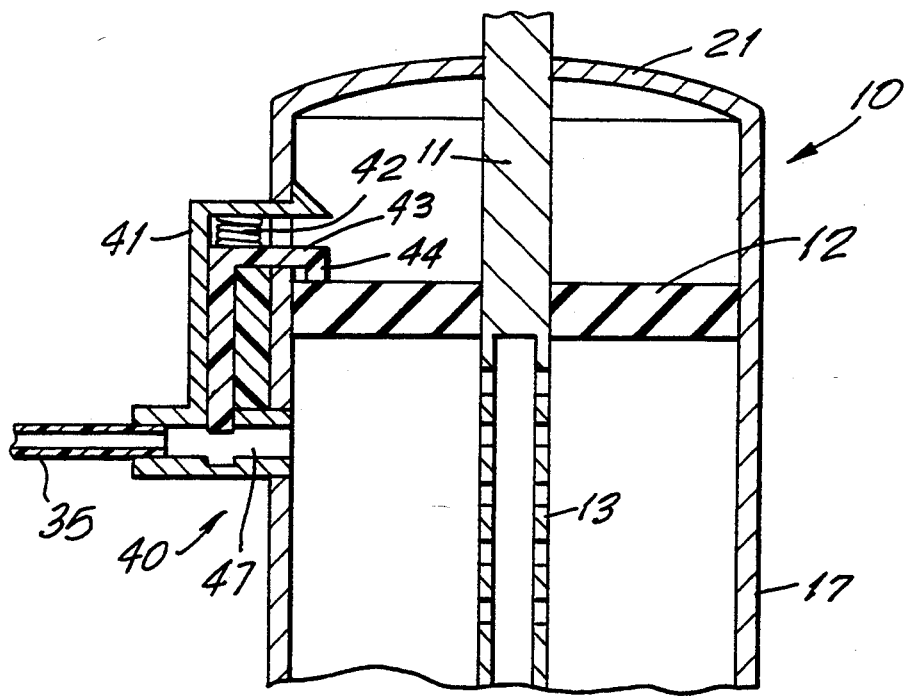
FIGS. 6 and 7 are enlarged cross-sectional views of the injector valve mechanism.
Figure 6:
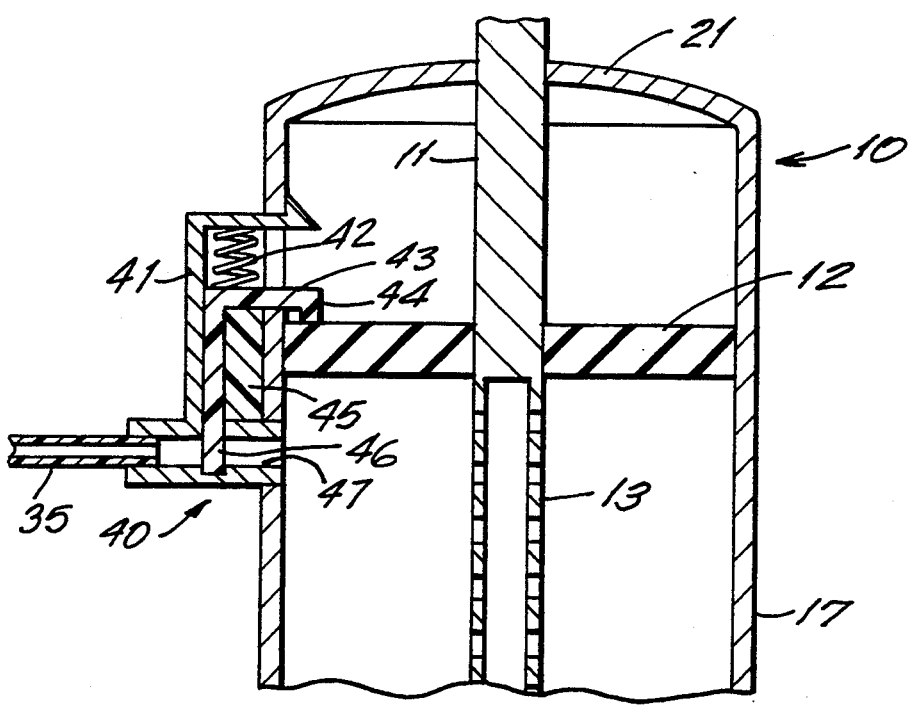

As shown in FIGS. 6 and 7, the fill line 35 terminates in a liquid valve 40 connected on the side of the injector 10. When the plunger 11 is fully withdrawn (pulled upright) its piston head 12 will open the valve 40 and the electrolyte will flow and fill up the injector electrolyte chamber 15.

In FIG. 6 the piston head 12 is down, when an electrode is being filled, and the valve 40 is closed. In FIG. 7, the plunger is withdrawn and the piston head 12 has opened the valve 40.

The valve 40 includes a valve casing 41 secured to the side of the injector plunger 10, a coil spring 42 which applies pressure to the top of the valve gate 43. An arm 44 of valve gate 43 is positioned on top of the head 12 so that upward movement of head 12 lifts the arm 44 and gate 43. The gate is guided by block 45 and its lower portion 46 normally closes the fluid passage 47.

The injector system may be used to fill various types of electrodes, examples of three types of EEG electrodes being shown in FIGS. 8–10B.

Figure 8:
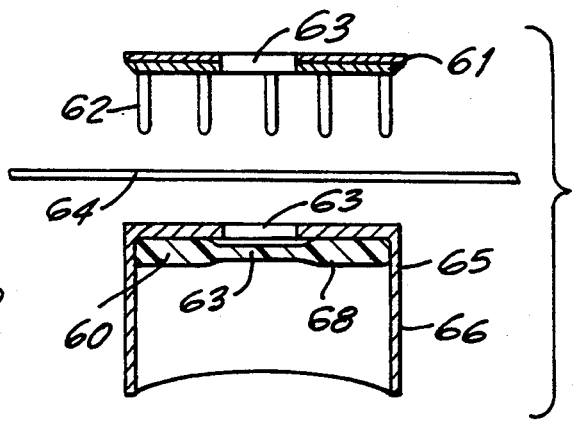
FIG. 8 is a side exploded cross-sectional view of an EEG electrode and holder.

In the electrode of FIG. 8, a metal washer-like electrode 60 and the plastic electrode holder 66 are held by a retainer 61 having eight posts 62. The electrode 60, electrode holder 66 and retainer 61 have a central aperture 63. The posts 62 protrude through the fabric of cap 64 and are held in the eight holes 65 of electrode holder 66. The bolus of electrolyte is deposited by the injector through aperture 63 to wet the surface 68 of the electrode 60.

Figure 9A:
FIG. 9A is a side view and FIG. 9B is a top view of an EEG electrode which fits into the holder of FIG. 8.
Figure 10A:
FIG. 10A is a side view and FIG. 10B is a top view of another type of EEG electrode.
Figure 9B:
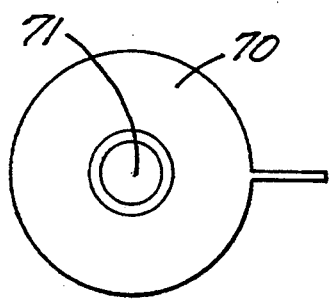
Figure 10B:
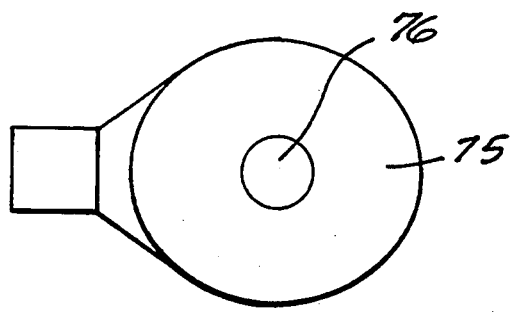

FIGS. 9A and 9B show a flat disk electrode 70 having an aperture 71. FIGS. 10A and 10B show a wet cut electrode 75 having a dome and an aperture 76.

Modifications may be made in the above-described system and device within the scope of the sub-joined claims. For example, the plunger may be spring-loaded by a coil compression spring within the injector so that the plunger is normally raised. The spreadable flaps 23 may be made as a removable sub-component for easy cleaning or replacement. The external electrolyte reservoir may be filled by a pressurized $CO_2$ cylinder and may be part of the injector assembly.

What is claimed is:

1. An electrolyte injector device to inject conductive fluid electrolyte into the cavity of an electrode adapted to be applied to the skin of a patient, the injector device comprising:
   a hollow body forming an enclosed chamber adapted to hold electrolyte, the body having a top portion with a top hole and a bottom portion with a bottom orifice;
   a plunger adapted to be finger-operated and protruding through the top hole, the plunger having a bottom end and having an injector head with an orifice at the bottom end;
   a piston fixed to the plunger and positioned to apply pressure within the chamber;
   the plunger having a hollow shaft portion with holes therein to allow flow of electrolyte from the chamber into the hollow shaft portion; and
   a block member fixed to the body top portion and having a bore therein in which the plunger slides, the block member closing the holes in the hollow shaft portion when the plunger is depressed;
   wherein the body bottom portion is flexible and has flexible flaps and the flaps are spread open by the injector head on depression of the plunger.

2. An injector device as in claim 1 wherein the body is cylindrical.

3. An injector device as in claim 1 wherein the bottom portion has a plurality of flexible flaps which are spread out by downward movement of the injector head and which part the hair on a scalp, providing an unobstructed pathway between the bottom portion and the scalp.

4. An injector device as in claim 3 wherein the plurality are four flexible flaps.

5. An injector device as in claim 1 and further including a valve means to control flow of electrolyte and operated by the piston to be opened when the plunger is raised and to be closed when the plunger is depressed.

* * * * *